United States Patent [19]

Asinger et al.

[11] 3,959,302

[45] May 25, 1976

[54] PROCESS FOR THE SPLITTING OF THE RACEMATE OF D-1-PHENYLPROPANOLAMINE

[75] Inventors: Friedrich Asinger, Aachen; Heribert Offermanns, Grossauheim, both of Germany

[73] Assignee: Deutsche Gold- und Silber-Scheideanstalt vormals Roessler, Germany

[22] Filed: Oct. 10, 1974

[21] Appl. No.: 513,725

Related U.S. Application Data

[63] Continuation-in-part of Ser. No. 419,448, Nov. 27, 1973, abandoned, and a continuation-in-part of Ser. No. 276,236, July 28, 1972, abandoned.

[30] Foreign Application Priority Data

July 30, 1971 Germany............................ 2138121
Nov. 29, 1972 Germany............................ 2258410

[52] U.S. Cl....................... 260/306.7 C; 260/570.6
[51] Int. Cl.[2].......................................... C07D 277/06
[58] Field of Search.................. 260/570.6, 306.7 C

[56] References Cited
UNITED STATES PATENTS

1,867,274   7/1932   Manske............................ 260/570.6

2,450,784   10/1948   Duffin et al...................... 260/306.7

OTHER PUBLICATIONS

Stewart, *Stereochemistry*, Lengmans, Green and Co., London, 1919, pp. 40–42.

*Primary Examiner*—Richard J. Gallagher
*Attorney, Agent, or Firm*—Cushman, Darby & Cushman

[57] ABSTRACT

The d,1-phenylpropanolamine(norephedrine) racemate is split with optically active thiazolidine-4-carboxylic acids of the formula:

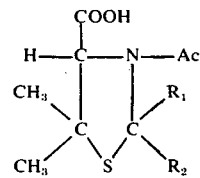

where $R_1$ and $R_2$ are both methyl or are joined together to form the pentamethylene group.

18 Claims, No Drawings

PROCESS FOR THE SPLITTING OF THE RACEMATE OF D-1-PHENYLPROPANOLAMINE

This application is a continuation-in-part of application Ser. No. 276,236, filed July 28, 1972 and now abandoned and is also a continuation-in-part of application Ser. No. 419,448 filed Nov. 27, 1973, now abandoned. The entire disclosure of the parent application is hereby incorporated by reference.

1-Phenylpropanolamine is an important starting material for the synthesis of medicines. It is recovered from molasses by fermentation processes. However, it is also known to produce 1-phenylpropanolamine by resolution of d,l-norephedrine with the help of optically active tartaric acid (Liebigs Annalen der Chemie, Vol. 470, pages 157-182). This process is not very satisfactory since the solubility differences of the diastereomer salts are too slight as a result of which multiple recrystallizations of the salts are necessary. As a result, the yields are very unsatisfactory.

As used hereinafter, the term phenylpropanolamine is used as is customary in the art to designate 1-phenyl-1-hydroxy-2-aminopropane as is shown for example in the above cited article from Liebigs Annalen and also as shown in Fieser and Fieser "Organic Chemistry," third edition (1956) pages 704 and 1098. Another name for 1-phenyl-1-hydroxy-2-aminopropane is norephedrine.

It is not possible to predict the ability of an acid to resolve a racemate of an optically active amine (or of an amine to resolve the racemate of an optically active acid). Thus, Eliel "Stereochemistry of Carbon Compounds" (1962), pages 49-50 points out that this can only be done by trial and error. As an illustration Eliel points out that while it might be thought that mandelic acid (alpha hydroxy beta phenylacetic acid) and atrolactic acid (alpha hydroxy alpha methyl beta phenylacetic acid) might be considered similar nevertheless ephedrine can resolve mandelic acid but not atrolactic acid.

Likewise Greenstein and Winitz "Chemistry of the Amino Acids," Vol. 1, pages 716–718 points out that the resolution procedure is rather empirical and that none of the conditions necessary for a successful resolution can be predicted a priori, and the resolution of each individual racemate constitutes a separate experimental problem.

It has now been found that there can be obtained optically active phenylpropanolamine(norephedrine) and especially 1-phenyl-propanolamine(1-norephedrine) in high yields and in high purity by resolution of d,l-phenylpropanolamine(d,l-norephedrine) with optically active acids if there is used as the optically active acid an optically active thiazolidine-4-carboxylic acid of the general formula:

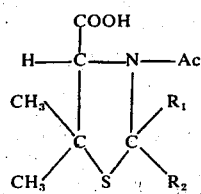

in which $R_1$ and $R_2$ are the same or different and are both methyl or are joined together to form the pentamethylene group and Ac is formyl.

The preferred optically active acid is 3-formyl-2,2,5,5-tetramethyl-thiazolidine-4-carboxylic acid. Correspondingly to recover 1-phenylpropanolamine(1-norephedrine) there is employed D-3-formyl-2,2,5,5-tetramethyl-thiazolidine-4-carboxylic acid.

As organic solvents for the reaction there can be used alcohols, halogenated aliphatic hydrocarbon, dioxane, ketones, esters, aromatic hydrocarbons, etc. There are preferably used benzene, toluene, isopropanol, dioxane and lower carboxylic acid esters, e.g., ethyl acetate.

Specific examples of additionally suitable solvents include methanol, ethanol, butanol, isooctyl alcohol, isodecyl alcohol, dodecyl alcohol, chloroform, carbon tetrachloride, dichloroethylene, 1,1,2,2-tetrachloroethane, dibromoethylene, acetone, methyl ethyl ketone, methyl butyl ketone, diethyl ketone, ethyl formate, ethyl propionate, methyl formate, ethyl formate, ethyl propionate, ethyl butyrate, propyl acetate, ethyl propionate.

In carrying out the process of the invention suitably d,l-phenyl-propanolamine(d,l-norephedrine) is dissolved in water or more preferably in an organic solvent such as those set forth above and this solution, in a given case with heating, treated with the optically active thiazolidine-4-carboxylic acid of formula I, in a given case dissolved in an organic solvent, e.g., any of the organic solvents set forth above. Thereupon frequently immediately, on occasion, however, only after long standing, in a given case at low temperatures and after inoculation (seeding), the difficultly soluble salt of the optically active amine and the optically active thiazolidine-4-carboxylic acid of general formula I precipitates. The diastereoisomeric salt, the optical antipode, remaining optically active adjuvant acid or racemic mixture or mixtures thereof remain in the mother liquor.

However, the reverse can occur and the solution of the optically active thiazolidine-4-carboxylic acid of general formula I in water or more preferably in an organic solvent be treated with the racemic mixture of phenylpropanolamine(norephedrine) which preferably is dissolved in an organic solvent, e.g., any of those set forth above.

According to the process of the invention there can be used 0.1 to 3 moles, preferably 0.5 to 1.1 moles of the optically active thiazolidine-4-carboxylic acid of general formula I per mole of racemate. In all ranges the more difficultly soluble salt of the optically active phenylpropanolamine and optically active thiazolidine-4-carboxylic acid precipitates out. This precipitation is nearly quantitative if the amounts of reactants are kept nearly stoichiometric. By the use of less than 0.5 mole of the thiazolidine-4-carboxylic acid per mole of phenyl-propanolamine racemate there remains in the mother liquor the racemate and optical antipode. If there is used per mole of racemate 0.5 to <1 mole of optically active thiazolidine-4-carboxylic acid, the mother liquor contains besides the optical antipode diastereoisomeric salt. If there is added per mole of racemate more than 1 mole of thiazolidine-4-carboxylic acid, there remains in the mother liquor in addition to the diastereoisomeric salt optically active thiazolidine-4-carboxylic acid.

The salt of the optically active phenylpropanolamine and the optically active thiazolidine-4-carboxylic acid of formula I resulting from the conversion can be recovered in pure form in known manner, because of its very favorable solubility differentiations, for example by filtration, evaporation of the mother liquor, purification by recrystallization. The splitting of the salt can be carried out in known manner by treating with preferably aqueous mineral acids, for example, hydrochloric acid, hydrobromic acid, sulfuric acid, phosphoric acid, whereby the mineral acid salt of the optically active base is formed and the optically active thiazolidine-4-carboxylic acid can be recovered in high yields.

If there are used non stoichiometric amounts of the optically active thiazolidine-4-carboxylic acid, it is possible to separate the difficultly soluble salt of the optically active amine and optically active thiazolidine-4-carboxylic acid from the diastereoisomeric salt, the racemic amine mixture and the optical antipode or their mixture because of the favorable solubility differentiation likewise in manner known in itself.

The process of the invention is especially suitable for the recovery of 1-phenylpropanolamine(1-norephedrine) using D-thiazolidine-4-carboxylic acids of formula I. The optically pure thiazolidine-4-carboxylic acids can be recovered from the racemic acid mixture in known manner, for example by using brucine (in the manner described in Duffin U.S. Pat. No. 2,450,784 or British Pat. No. 585,413), preferably, however, using for example 1-phenylpropanol-amine(1-norephedrine) produced by fermentation and recovered from the racemic mixture.

The thiazolidine-4-carboxylic acid of formula I can be produced for example by the process described in Belgian Pat. No. 738,520.

Unless otherwise indicated, all parts and percentages are by weight.

EXAMPLE 1

21.7 gram (0.1 mole) of D-3-formyl-2,2,5,5-tetramethyl-thiazolidine-4-carboxylic acid were dissolved in 150 ml of ethyl acetate with heating and mixed at about 70°C. with a solution of 15.1 grams (0.1 mole) of d,l-phenylpropanolamine(d,l-norephedrine) in 45 ml of ethyl acetate. After a short time the salt of 1-phenylpropanolamine(1-norephedrine) and D-3-formyl-2,2,5,5-tetramethyl-thiazolidine-4-carboxylic acid precipitated out. After 30 minutes heating at reflux and cooling to room temperature the product was filtered off with strong suction and washed with 20 ml of ethyl acetate. After drying at 45°C. under reduced pressure there were obtained 17.5 grams (95%) of the salt melting at 198°–199°C.; $[\alpha]_D^{20} + 36°$. The salt was treated at room temperature with 80 ml of dilute hydrochloric acid (1:10). There were obtained after filtering with suction 9.7 grams (90%) of D-3-formyl-2,2,5,5-tetramethyl-thiazolidine-4-carboxylic acid with $[\alpha]_D^{20} + 51°$ as the constituent insoluble in the dilute hydrochloric acid. From the mother liquor there were obtained 9.2 grams (98%) of 1-phenylpropanolamine.HCl(1-norephedrine.HCl) which after a single recrystallization from isopropyl alcohol melted at 164°C.; $[\alpha]_D^{20} - 36°$. After evaporation of the mother liquor of racemic splitting to dryness there were obtained 18 grams (96%) of the salt of d-phenylpropanolamine(d-norephedrine) and D-3-formyl-2,2,5,5-tetramethyl-thiazolidine-4-carboxylic acid. By splitting of the salt which was carried out in a manner analogous to that described, there was obtained 6.2 grams (66.5%) of d-phenylpropanolamine.HCl(d-norephedrine.HCl), that after recrystallization from isopropyl alcohol melted at 158°C.; $[\alpha]_D^{20} + 35.4°$.

EXAMPLE 2

21.7 grams (0.1 mole) of D-3-formyl-2,2,5,5-tetramethyl-thiazolidine-4-carboxylic acid were dissolved in 150 ml of ethyl acetate with heating to 50°C. and mixed with a solution of 30.2 grams (0.2 mole) of d,l-phenylpropanolamine(d,l-norephedrine) in 150 ml of ethyl acetate at this temperature. After heating for 20 minutes under reflux and subsequently cooling to room temperature the product was filtered off with strong suction and subsequently washed with 30 ml of ethyl acetate. There were obtained 34.7 grams (95%) of the salt of 1-phenylpropanolamine(1-norephedrine) and D-3-formyl-2,2,5,5-tetramethyl-thiazolidine-4-carboxylic acid melting at 193°C.; $[\alpha]_D^{20} + 35.8°$.

The splitting of the salt which was carried out as described in example 1 resulted in 15.4 grams (71%) of D-3-formyl-2,2,5,5-tetramethyl-thiazolidine-4-carboxylic acid as well as 15 grams (82%) of 1-phenylpropanolamine.HCl(1-norephedrine.HCl) having the melting point 165°C.; $[\alpha]_D^{20} - 32°$. From the mother liquor of the racemate splitting there were obtained after evaporation to dryness and treatment with isopropanolic HCl 12 grams (65%) of d-phenylpropanolamine.HCl(d-norephedrine.HCl) having $[\alpha]_D^{20} + 35.5°$.

EXAMPLE 3

60.4 grams (0.4 mole) of d,l-phenylpropanolamine (d,l-norephedrine) were dissolved in 500 ml of ethyl acetate with heating. To this solution there were added dropwise inside 20 minutes a solution of 43.4 grams (0.2 mole) of L-3-formyl-2,2,5,5-tetramethylthiazolidine-4-carboxylic acid in 100 ml of ethyl acetate. After 30 minutes heating under reflux and cooling to room temperature the product was filtered off with strong suction and there were obtained 70 grams (95%) of the salt of d-phenylpropanolamine(d-norephedrine) and L-3-formyl-2,2,5,5-tetramethyl-thiazolidine-4-carboxylic acid that after a single recrystallization from isopropanol melted at 203°C.; $[\alpha]_D^{20} - 34.3°$. 61 grams of this salt were split in a manner analogous to that described in Example 1. There were obtained 33 grams of L-3-formyl-2,2,5,5-tetramethyl-thiazolidine-4-carboxylic acid melting at 179°–180°C.; $[\alpha]_D^{20} - 54.4°$ as well as 26.5 grams of d-phenylpropanolamine. HCl(d-norephedrine.HCl) melting point 173°C.; $[\alpha]_D^{20} + 33°$. From the mother liquor of the racemate splitting by evaporation to dryness and treatment with isopropanolic HCl there were obtained 28 grams (77%) of 1-phenylpropanolamine.HCl(1-norephedrine.HCl), melting point 179°C.; $[\alpha]_D^{20} - 31.4°$.

EXAMPLE 4

The procedure of Example 1 was employed except that acetone was used as the solvent for the splitting of the racemate. There was obtained the salt of 1-phenylpropanolamine(1-norephedrine) and D-3-formyl-2,2,5,5-tetramethyl-thiazolidine-4-carboxylic acid in a yield of 84%, melting point 201°C.; $[\alpha]_D^{20} + 32.8°$.

EXAMPLE 5

The procedure of Example 1 was employed except that isopropyl alcohol was used as the solvent. There was obtained the salt of 1-phenylpropanolamine(1-norephedrine) and D-3-formyl-2,2,5,5-tetra-methylthiazolidine-4-carboxylic acid in a yield of 81%. Melting point 201°C.; $[\alpha]_D^{20} + 34.1°$.

EXAMPLE 6

The procedure of Example 1 was employed except that dioxane was used as the solvent. There was obtained the salt of 1-phenylpropanolamine(1-norephedrine) and D-3-formyl-2,2,5,5-tetramethyl-thiazolidine-4-carboxylic acid in a yield of 72%. Melting point 197°C.; $[\alpha]_D^{20} + 32.8°$.

EXAMPLE 7

43.5 grams (0.2 mole) of D,L-3-formyl-2,2,5,5-tetramethyl-thiazolidine-4-carboxylic acid were dissolved in 300 ml of ethyl acetate with heating and mixed with a solution of 33.3 grams (0.22 mole) of 1-phenyl-propanolamine(1-norephedrine) (recovered from molasses by fermentation) dissolved in 100 ml of ethyl acetate. After heating for 30 minutes under reflux the mixture was cooled, filtered off with strong suction and subsequently washed with 100 ml of ethyl acetate. There were obtained 34.6 grams (94%) of the salt of 1-phenyl-propanolamine(1-norephedrine) and D-3-formyl-2,2,5,5-tetramethyl-thiazolidine-4-carboxylic acid melting at 197°–200°C.; $[\alpha]_D^{20} + 30°$. The splitting of this salt was carried out in a manner analogous to Example 1 and resulted in the formation of 19.4 grams (89%) of D-3-formyl-2,2,5,5-tetramethyl-thiazolidine-4-carboxylic acid melting at 179°–181°C.; $[\alpha]_D^{20} + 54°$. The 1-phenyl-propanolamine(1-norephedrine) can be recovered from the mother liquor of the splitting of the salt. After evaporation to dryness of the mother liquor from the splitting of the racemate and treating the residue obtained thereby with isopropyl alcohol there were obtained 35.3 grams (96%) of the salt of L-3-formyl-2,2,5,5-tetramethyl-thiazolidine-4-carboxylic acid and 1-phenylpropanolamine (1-norephedrine) which was split in an analogous manner to the diastereomeric salt. There were recovered 20.4 grams (97%) of L-3-formyl-2,2,5,5-tetramethyl-thiazolidine-4-carboxylic acid melting at 179°–180°C.; $[\alpha]_D^{20} -54°$.

EXAMPLE 8

The procedure of Example 1 was employed except there were used 30.2 grams (0.2 mol) of d,l-norephedrine and 51.4 grams (0.2 mol) of D-3-formyl-2,2-pentamethylene-5,5-dimethylthiazolidine-4-carboxylic acid in place of the 2,2,5,5-tetramethyl compound. The salt of 1-norephedrine and D-3-formyl-2,2-pentamethylene-5,5-dimethyl-thiazolidine-4-carboxylic acid recovered had a melting point of 190°–191°C. and a specific rotation of +25.5°. The splitting of the salt was carried out in the manner described in Example 1. Thereby there were recovered 18 grams of D-3-formyl-2,2-pentamethylene-5,5-dimethyl-thiazolidine-4-carboxylic acid, corresponding to 70%. The yield of 1-norephedrine hydrochloride amounted to 14.5 grams corresponding to 76%. The melting point was 164° – 165°C., the specific rotation was −32.5°.

EXAMPLE 9

The procedure of Example 1 was employed except that there were used 30.2 grams (0.2 mol) of d,l-norephedrine and 25.7 grams (0.1 mol) of D-3-formyl-2,2-pentamethylene-5,5-dimethyl-thiazolidine-4-carboxylic acid. The recovered salt of 1-norephedrine and D-3-formyl-2,2-pentamethylene-5,5-dimethyl-thiazolidine-4-carboxylic acid had a specific rotation of +26° and a melting point of 189°–191°C. The yield was 32 grams, corresponding to 78%.

By replacing the D-3-formyl-2,2-pentamethylene-5,5-dimethyl-thiazolidine-4-carboxylic acid with L-3-formyl-2,2-pentamethylene-5,5-dimethyl-thiazolidine-4-carboxylic acid there is recovered the salt of d-norephedrine.

What is claimed is:

1. An optically active salt of norephedrine with a thiazolidine-4-carboxylic acid of the formula:

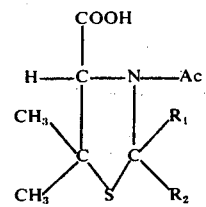

where $R_1$ and $R_2$ are both methyl and Ac is formyl.

2. An optically active salt according to claim 1 which is the salt of 1-norephedrine and the D form of the thiazolidine-4-carboxylic acid.

3. An optically active salt according to claim 1 which is the salt of d-norephedrine and the L-form of the thiazolidine-4-carboxylic acid.

4. A process of splitting the racemate of d,l-phenyl-propanolamine comprising heating d,l-phenyl-propanol-amine in water or an organic solvent with an optically active form of a thiazolidine-4-carboxylic acid of the formula

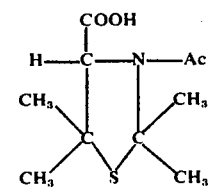

to form the salt of claim 1 in optically active form and then splitting said salt to the optically active form of phenylpropanolamine.

5. A process according to claim 4 wherein the salt is split with a mineral acid.

6. A process according to claim 4 for the recovery of 1-norephedrine comprising using as the optically active acid the D form of the thiazolidine-4-carboxylic acid.

7. A process according to claim 4 wherein the d,l-norephedrine is employed as a solution in an alcohol, halogenated aliphatic hydrocarbon, ketone, ester, aromatic hydrocarbon or dioxane and the optically active form of the thiazolidine-4-carboxylic acid is employed in solution in an alcohol, halogenated aliphatic hydrocarbon, ketone, ester, aromatic hydrocarbon or dioxane, the salt of the optically active 1-norephedrine and optically active thiazolidine-4-carboxylic acid formed is separated off and then split.

8. A process according to claim 7 wherein the splitting of said salt is done with aqueous mineral acid and the mineral acid salt of d or 1-norephedrine formed is isolated.

9. A process according to claim 8 wherein there is used 0.1 to 3 moles of optically active thiazolidine-4-carboxylic acid per mole of racemate.

10. A process according to claim 9 wherein there is used 0.5 to 1.1 mole of thiazolidine-4-carboxylic acid per mole of racemate.

11. An optically active salt according to claim 2 in solid form and free of the salt of l-norephedrine and the L form of the thiazolidine-4-carboxylic acid.

12. A process of splitting the racemate of d,l-phenylpropanolamine comprising heating d,l-phenylpropanolamine in water or an organic solvent with an optically active form of a thiazolidine-4-carboxylic acid of the formula

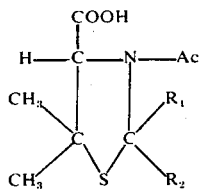

where $R_1$ and $R_2$ are joined together to form the pentamethylene group to form the salt of phenylpropanolamine and said thiazolidine-4-carboxylic acid in optically active form and then splitting said salt to the optically active form of phenylpropanolamine.

13. A process according to claim 12 wherein the salt is split with a mineral acid.

14. A process according to claim 12 for the recovery of l-norephedrine comprising using as the optically active acid the D form of the thiazolidine-4-carboxylic acid.

15. A process according to claim 12 wherein the d,l-norephedrine is employed as a solution in an alcohol, halogenated aliphatic hydrocarbon, ketone, ester, aromatic hydrocarbon or dioxane and the optically active form of the thiazolidine-4-carboxylic acid is employed in solution in an alcohol, halogenated aliphatic hydrocarbon, ketone, ester, aromatic hydrocarbon or dioxane, the salt of the optically active l-norephedrine and optically active thiazolidine-4-carboxylic acid formed is separated off and then split.

16. A process according to claim 15 wherein the splitting of said salt is done with aqueous mineral acid and the mineral acid salt of d or l-norephedrine formed is isolated.

17. A process according to claim 16 wherein there is used 0.1 to 3 moles of optically active thiazolidine-4-carboxylic acid per mole of racemate.

18. A process according to claim 17 wherein there is used 0.5 to 1.1 mole of thiazolidine-4-carboxylic acid per mole of racemate.

* * * * *